United States Patent [19]

Mehta

[11] Patent Number: 4,820,672

[45] Date of Patent: Apr. 11, 1989

[54] HYDROCARBON SOLUBLE AND INSOLUBLE ORGANO MAGNESIUM CHLORIDE COMPLEXES, PROCESSES AND USES

[75] Inventor: Vijay C. Mehta, Gastonia, N.C.

[73] Assignee: Lithium Corporation of America, Gastonia, N.C.

[21] Appl. No.: 192,750

[22] Filed: May 9, 1988

Related U.S. Application Data

[63] Continuation-in-part of Ser. No. 67,061, Jun. 25, 1987, abandoned.

[51] Int. Cl.$^4$ .............................................. B01J 31/26
[52] U.S. Cl. ........................................ 502/115; 264/5; 423/497; 423/507; 502/118; 502/119; 502/134; 502/172; 526/125; 568/851
[58] Field of Search ............... 502/115, 118, 119, 134, 502/172; 423/497, 507; 526/125; 264/5; 568/851

[56] References Cited

U.S. PATENT DOCUMENTS

| | | | |
|---|---|---|---|
| 3,471,250 | 10/1969 | Langer | 423/497 |
| 4,056,599 | 11/1977 | Fox, III et al. | 423/497 |
| 4,315,874 | 2/1982 | Ushida et al. | 264/5 |
| 4,370,455 | 1/1983 | Ueda et al. | 526/125 |
| 4,399,054 | 8/1983 | Ferraris et al. | 252/429 B |
| 4,520,121 | 5/1985 | Inkrot et al. | 502/119 |
| 4,562,168 | 12/1985 | Lee | 502/119 |
| 4,567,153 | 1/1986 | Graves | 502/134 |
| 4,613,579 | 9/1986 | Furuhashi et al. | 526/132 |
| 4,622,309 | 11/1986 | Coleman et al. | 502/119 |
| 4,693,990 | 9/1987 | Hiroyuki et al. | 502/118 |
| 4,727,049 | 2/1988 | Furuhashi et al. | 502/115 |

FOREIGN PATENT DOCUMENTS

| | | | |
|---|---|---|---|
| 0022675 | 1/1981 | European Pat. Off. | 526/125 |
| WO86/00314 | 1/1987 | United Kingdom | 526/125 |

*Primary Examiner*—Anthony McFarlane
*Attorney, Agent, or Firm*—Charles C. Fellows; Robert L. Andersen

[57] ABSTRACT

A process for producing an alcohol adducted or complexed hydrocarbon soluble magnesium chloride comprising reacting in a hydrocarbon medium a compound selected from magnesium metal, dialkyl magnesium, dialkoxy magnesium and alkoxy magnesium chloride with a dry hydrogen halide and a $C_1$ to $C_{10}$ chloro-alcohol or mixtures of chloro-alcohol and a $C_5$ to $C_{18}$ beta-alkyl substituted alcohol which may optionally contain some $C_1$ to $C_{20}$ primary unsubstituted monohydric alcohol.

37 Claims, No Drawings

HYDROCARBON SOLUBLE AND INSOLUBLE ORGANO MAGNESIUM CHLORIDE COMPLEXES, PROCESSES AND USES

This application is a continuation in part of U.S. Ser. No. 067,061 filed June 25, 1987, now abandoned.

This invention concerns a method for making novel hydrocarbon soluble and insoluble magnesium chloride compositions in which magnesium chloride is adducted or complexed with an alcohol, may or may not contain a transition metal, and which complexes are useful in manufacturing high performance alpha-olefin polymerization catalysts.

Activated magnesium chloride has long been important in the manufacture of high performance catalysts for making polyethylene and polypropylene. Anhydrous magnesium chloride is activated commercially by mechanical and chemical methods. As early as 1967, C. W. Kamienski (Univ. Microfilms, Ann Arbor, Mich., 68–9810) reported that commercial anhydrous magnesium chloride could be activated by treatment with alcohols or ethers. Commercial anhydrous magnesium chloride contains impurities which cannot easily be removed. Polymer manufacturers therefore use synthetic routes to $MgCl_2$ as they attempt to obtain 100% active $MgCl_2$. There exists a large number of patents concerning use of magnesium chloride from one source or another in the manufacture of Ziegler-Natta (Z/N) olefin polymerization catalysts.

The Z/N catalysts seem to include every combination of a transition metal compound and an organometallic compound from groups I to III of the periodic table that will promote olefin polymerization. Magnesium precursors such as dialkyl magnesium, magnesium dialkoxides, alkyl magnesium alkoxides, alkoxy magnesium chloride and the like are being tested and some used extensively for preparing supported Z/N catalysts for polyolefin production. Although magnesium diethoxides (alkoxides) and commercial anhydrous magnesium chloride are the most extensively used solid magnesium precursors, many other magnesium precursors in solid and soluble form have been transformed by various treatments into activated magnesium chloride catalyst supports. Typically alpha-olefins are polymerized in fluid-bed reactors.

Recently there has been an interest in preparing hydrocarbon soluble magnesium chloride precursors such as organic magnesium compounds which can be reacted with transition metal chlorides. Generally, the organic magnesium compounds are reacted with a chlorinating agent to convert them to $MgCl_2$, wherein the transition metal compound is deposited on the $MgCl_2$. This reaction apparently produces a catalyst of fine, uniform size consisting of the transition metal deposited on finely divided magnesium chloride. The organic portion of the organo-magnesium compound is generally wasted in this type of process.

One approach to producing magnesium chloride suitable for use in preparing Z/N type catalysts is to make alcohol adducted magnesium chloride from commercially available anhydrous magnesium chloride. These magnesium chloride adducts are then used in preparing Z/N catalysts. This approach is exemplified in U.S. Pat. Nos. 4,071,674; 4,315,474; 4,399,054; British Pat. No. 1,271,411; and German Pat. No. 2,346,71 in which alcohol adducted magnesium chloride was made using anhydrous magnesium chloride and alcohols, primarily ethanol.

Takashi Ueda et al. (U.S. Pat. No. 4,370,455, 1983) describe polymerization or copolymerization of olefins in the presence of a catalyst composed of (a) solid $MgCl_2$ obtained by reacting (1) an adduct between commercial anhydrous $MgCl_2$ and an electron donor selected from the group consisting of an alcohol with b 1 to 18 carbon atoms, an aldehyde with 2 to 15 'C' atoms, a carboxylic acid with 2 to 18 'C' atoms and an amine, with (2) an organoaluminum compound and followed by reaction with (b) a transition metal compound and (c) an organoaluminum compound. In one example, anhydrous solid $MgCl_2$ is solubilized in kerosene by using 3 moles of 2-ethyl-hexanol per mole of $MgCl_2$.

Yoshihisa Ushida in U.S. Pat. No. 4,315,874 disclosed a process of producing spherical particles of solid magnesium chloride adducted by ethanol. The process formed a suspension of molten droplets of ethanol adducted anhydrous magnesium chloride in an organic liquid medium in the presence of at least one oil soluble surface active agent by quenching hot suspended molten droplets to solidify adducted magnesium chloride into spherical particles. The spherical magnesium chloride particles were reacted with organometallic compounds and a transition metal compound to obtain an olefin polymerization catalyst.

Ferraris et al. in U.S. Pat. No. 4,399,054 disclosed preparation of spherical particles of alcohol adducted anhydrous magnesium chloride having a narrow particle size distribution range. Anhydrous magnesium chloride with ethanol in a 1:3 mole ratio was heated in vaseline oil to 120° C. The magnesium chloride melted and remained mixed in the vaseline oil. This mixture was dispersed in anhydrous heptane and cooled initially to $-40°$ C. with the final temperature of the mix adjusted to 0° C. The spheroidal solid product, $MgCl_2:2.7C_2H_5OH$, contained 94.1% particles of less than 50$\mu$ (micron) size. These particles were reacted with a transition metal compound and an organoaluminum compound to produce an olefin catalyst. Polymers produced by use of this catalyst were spherical and had a flowability of 12 to 15 seconds.

Finely ground "anhydrous" magnesium chloride has been extensively used in making Z/N olefin polymerization catalysts but unfortunately commercially available "anhydrous" magnesium chloride always retains some water; handling this magnesium chloride usually adds additional water and the water, though a rather small amount, results in forming undesirable oxychlorides on heating at high temperatures to remove the water.

The literature indicates that magnesium precursors such as dialkyl magnesium, magnesium dialkoxides, alkylmagnesium alkoxides and alkoxy magnesium chloride are being evaluated and in some instances used extensively for preparing Z/N olefin catalysts. Nevertheless, polyolefin manufacturers continue to search for and evaluate effective soluble and insoluble magnesium compounds and complexes.

The present invention provides hydrocarbon soluble and insoluble complexes of magnesium chloride and up to 6 moles of a chloro-alcohol containing one to ten carbon atoms and mixtures of a $C_1$ to $C_{10}$ chloro-alcohol and a $C_5$ to $C_{18}$ beta-alkyl substituted primary, secondary or tertiary alcohol containing and which mixtures may also contain a $C_1$ to $C_{20}$ unsubstituted primary monohydric alcohol and a method of producing such complexes which may or may not contain a transition metal. When the complexes are prepared from a chloro substituted alcohol or a beta-alkyl substituted primary or secondary alcohols, the complexes may or may not be hydrocarbon solvent soluble. Use of excess $C_1$ to $C_{10}$ chloro-alcohol or mixtures with $C_5$ to $C_{18}$ beta-alkyl substituted alcohols produce solutions. Use of less than 2.5 moles, often less than 2 moles, of alcohol or chloro-alcohol or mixtures thereof produce solutions of the complex at 50° C. or above which solution can be used to precipitate narrow range particle size, less than 50 μm, of uniform spherical shape products by using a simple temperature differential precipitation technique. When only normal unsubstituted alcohols (without chloro substituted alcohol or beta-alkyl substituted alcohols) are used in the process of this invention the complexes are not soluble in an ether free hydrocarbon solvent.

In accordance with one aspect of the present invention, there is provided a process for making hydrocarbon soluble and hydrocarbon insoluble magnesium chloride-alcohol complexes in which the source of magnesium is a reactant selected from magnesium metal, a dialkyl magnesium, an alkoxymagnesium chloride or a magnesium dialkoxide. The magnesium metal or magnesium compound is reacted with a halogen containing compound or compounds selected from lower alkylhalides and/or hydrogen halides or a mixture thereof in a low boiling hydrocarbon solvent which contains an alcohol or a chloro-alcohol or to which an alcohol is added during or after formation of the magnesium dihalide.

The hydrocarbon soluble magnesium halide-alcohol complexes are based on mixtures with beta-alkyl substituted, primary, secondary and tertiary alcohols in solvating the magnesium halide complexes. One process aspect of this invention reacts in an ether free hydrocarbon solvent a dialkyl magnesium compound such as di-n-butyl magnesium with an anhydrous hydrogen halide such as hydrogen chloride while simultaneously adding to the reaction a chloro-alcohol or a mixture with a beta-alkyl substituted alcohol such as 2-methyl-1-pentanol in which the ratio of alcohol to magnesium halide is optimized at 3.2 moles of alcohol per mole of magnesium halide. Another process aspect reacts, in an ether free hydrocarbon solvent, magnesium metal, preferably iodine activated, with anhydrous hydrogen halide in the presence of a chloro-alcohol or a mixture with a beta-alkyl substituted alcohol. Another variation of the reaction aspect of this invention first reacts magnesium metal with a lower alkylhalide in an ether free hydrocarbon solvent followed by reacting the first reaction product with anhydrous hydrogen halide and then adding the chloro-alcohol or mixture thereof with a beta-alkyl substituted alcohol.

In a further process aspect of this invention, a chloro-alcohol or a beta-alkyl substituted magnesium alkoxide is reacted in a hydrocarbon solvent with an anhydrous hydrogen halide in the presence of an added amount of a beta-alkyl substituted alcohol usually the same alcohol from which the alkoxide was prepared. Optionally, an alkoxy magnesium chloride can be used in place of the magnesium dialkoxide.

The magnesium halide chloro-alcohol and mixtures with beta-alkyl substituted alcohol complexes of this invention are hydrocarbon soluble when prepared using at least 3.2 moles of alcohol per mole of magnesium chloride; however, these products can be produced as solid products by limiting the available amount of beta-alkyl substituted alcohol. For example, when desired, making $MgCl_2$ 2-methyl-1-pentanol complexes limiting the excess 2-methyl-1-pentanol to less than 3.0 moles results in a solid complex being precipitated.

The size, shape and particle size distribution of the product can be varied by controlling the agitation and cooling rate during precipitation of the particulate product. Generally, a precipitated product is separately produced then dispersed in a hydrocarbon solvent and the dispersion heated to redissolve the complex. The heated solution is then cooled under controlled conditions to precipitate a catalyst support. A catalytic material, such as titanium tetrachloride, can be added to the heated hydrocarbon solution of the complex and a catalytic material precipitated by cooling the solution. Thus, a catalyst or catalyst support having certain desired particle size, generally less than 100 μm and preferably less than 50 μm, and uniform particle size distribution and shape can easily be produced. Various techniques are known to affect particle size, shape and uniformity. For example, rapidly cooling a heated, generally saturated solution while agitating the solution with an agitator blade operating at a right angle to a vertical drive shaft, at high speed tends to produce very small nearly spherical particles of less than about 50 μm size; tilting such an agitator and operating at low speed and slow cooling produces spheroidal particles having uniform particle size distribution of less than 50 μm, typically about 0.1 to 25 μm, average particle size of about 5 to about 15 μm by scanning electron microscope (SEM) methodology and a BET surface area (ASTM C819-77) of between about 1 to about 5 square meters per gram.

The novel products of this invention include hydrocarbon soluble magnesium chloride/alcohol complexes with chloro-alcohols which may be mixed with a beta-alkyl substituted primary, secondary or tertiary alcohol. The product may be in the form of a hydrocarbon solution provided there is excess alcohol present beyond that required to form the complex. For example, when the alcohol selected is 2-methyl-1-pentanol and the hydrocarbon solvent is heptane, greater than 2.5 moles of alcohol are necessary to solvate the complex at room temperature; at higher temperatures, less alcohol is necessary to solvate the complex in a hydrocarbon solvent.

Beta-alkyl substituted primary monohydric (normal) alcohols or alkanols ($C_5$-$C_{18}$), which are complexed with a magnesium halide compound in various embodiments of this invention, and which surprisingly are hydrocarbon soluble, are exemplified by 2-methyl-1-pentanol, 2-methyl-1-butanol, 2-ethyl-1-butanol, 2-ethyl-1-pentanol, 2-ethyl-1-hexanol, 2-ethyl-4-methyl-1-pentanol, 2-propyl-1-heptanol, 2-methyl-1-hexanol, 2-ethyl-5-methyl-1-octanol, 2,2-dimethyl-1-octanol, and the like, or mixtures thereof. Particularly important beta(2)-alkyl substituted primary monohydric normal alcohols are 2-methyl-1-pentanol and 2-ethyl-1-hexanol and mixtures thereof.

Beta-alkyl substituted $C_5$-$C_{18}$ acyclic secondary alcohols; i.e., those secondary alcohols bearing at least one $C_1$-$C_4$ alkyl branch at the carbon atom beta to the hydroxyl group, which are complexed with a magnesium halide compound in various embodiments of this invention, which are surprisingly hydrocarbon soluble, are exemplified by 2-methyl-3-pentanol, 2,2-dimethyl-3-pentanol, 2,4-dimethyl-3-pentanol, 3-methyl-2-pentanol, 3-methyl-2-butanol, 4-methyl-3-hexanol, 3-methyl-2- hexanol, 2,4-dimethyl-3-hexanol, 3,4-dimethyl-2-hexanol, 2,4-dimethyl-3-heptanol, 4-methyl-3-heptanol, 2-methyl-3-octanol, 2,2-dimethyl-3-octanol, and the like. Also contemplated are beta-alkyl substituted cyclic $C_6$–$C_{18}$ secondary alcohols such as 2-methylcyclopentanol, 2-methylcyclohexanol, 2,6-dimethylcyclohexanol, 2-tertbutylcyclohexanol, and the like. Most preferred are those cyclic secondary alcohols bearing at least two beta methyl groups or one beta-tert-butyl group relative to the hydroxyl moiety.

Beta-alkyl substituted $C_6$–$C_{18}$ cyclic or acyclic tertiary alcohols; i.e., those tertiary alcohols bearing at least one $C_1$–$C_4$ alkyl branch at the carbon atom beta to the hydroxyl group which are complexed with a magnesium halide compound and which are unexpectedly hydrocarbon soluble, are exemplified by 2,3-dimethyl-2-butanol, 2,3-dimethyl-2-pentanol, 2,3-dimethyl-3-pentanol, 2,3-dimethyl-2-hexanol, 3,4-dimethyl-4-heptanol, 2,3,4-trimethyl-3-pentanol, 3,4,4-trimethyl-3-hexanol, 1,2-dimethylcyclopentanol, 1,2,6-trimethylcyclohexanol, and the like.

Other, less preferable $C_6$–$C_{18}$ secondary and tertiary cyclic and acyclic alcohols which are complexed with a magnesium halide compound in a further embodiment of this invention are those alcohols bearing alkyl group substitution further than the beta position from the carbon atom bearing the hydroxyl group; e.g., on the gamma or delta carbons. Examples of such alcohols which surprisingly are hydrocarbon soluble are 4-methyl-2-pentanol, 5-methyl-3-hexanol, 2,6-dimethyl-4-heptanol, 2-methyl-4-octanol, 3,5-dimethyl-3-hexanol, 2,6,8-trimethyl-4-nonanol, and 3-methylcyclohexanol.

Chloro-substituted alcohols containing 1 to 10 carbon atoms useful in practicing this invention and which most surprisingly are hydrocarbon soluble include but are not limited to 3-chlorobenzynol, 2-chlorobenzynol, 4-chlorobenzynol, 4-chloro-1-butanol, 2-chlorocyclohexanol, 3-chloro-2-2-dimethyl-1-propanol, 2-chloroethanol, 2-(2-chloroethoxy)ethanol, 2-[2-(2-chloroethoxy)ethoxy]ethanol, 2-chlorophenol, 2-chlorophenethyl alcohol, 1-chloro-2-propanol, 2-chloro-1-propanol, 3-chloro-1-propanol, etc.

Unsubstituted primary monohydric alcohols or alkanols ($C_1$ to $C_{20}$), which are complexed with a magnesium halide compound in various of the embodiments of this invention are exemplified by methanol, ethanol, propanol, butanol, pentanol, hexyl alcohol, heptyl and higher saturated alcohols ($C_8$ to $C_{20}$). When a chloro-substituted alcohol is used some unsubstituted monohydric alcohol can be used with the chloro-substituted alcohol to form soluble, liquid magnesium chloride complexes.

One aspect of the present invention utilizes a soluble magnesium halide of this invention dissolved in a hydrocarbon solvent together with a compound of a metal selected from Groups IV-B and V-B of the Periodic Table of the Elements. Preferred metal compounds are those of titanium, vanadium and zirconium. Examples of the titanium compound used in the present invention include halides, alkoxyhalides, alkoxides and halogenated oxides, of titanium. As preferred examples of the titanium compound, there may be mentioned tetravalent and trivalent titanium compounds. As tetravalent titanium compounds, those represented by the general formula $Ti(OR)_yX_{4-y}$ are preferred wherein R is a hydrocarbon radical such as an alkyl, aryl or aralkyl group having 1 to 24 carbon atoms, X is a halogen atom and $0 \leq y \leq 4$, such as titanium tetrachloride, titanium tetrabromide, titanium tetraiodide, monoethoxytrichlorotitanium, dimethoxydichlorotitanium, trimethoxymonochlorotitanium, tetramethoxytitanium, monoethoxytrichlorotitanium, diethoxydichlorotitanium, triethoxymonochlorotitanium, tetraethoxytitanium, monoisopropoxytrichlorotitanium, diisopropoxydichlorotitanium, triisopropoxymonochlorotitanium, tetraisopropoxytitanium, monobutoxytrichlorotitanium, dibutoxydichlorotitanium, monopentoxytrichlorotitanium, monophenoxytrichlorotitanium, diphenoxydichlorotitanium, triphenoxymonochlorotitanium and tetraphenoxytitanium. As trivalent titanium compounds, there may be used, for example, titanium trihalides obtained by reducing titanium tetrahalides such as titanium tetrachloride and titanium tetrabromide with hydrogen, aluminum, titanium or an organometallic compound of a Group I–III metal in the Periodic Table, as well as trivalent titanium compounds obtained by reducing tetravalent alkoxytitanium halides represented by the general formula $Ti(OR)_sX_{4-s}$ with an organometallic compound of a Group I–III metal in the Periodic Table, in which formula R is a hydrocarbon radical such as an alkyl, aryl or aralkyl group having 1 to 24 carbon atoms, X is a halogen atom and $0 < s < 4$.

In yet another aspect of this invention, not more than 2.5 moles of alcohol are employed per mole of magnesium-chloride to produce the complex in a hydrocarbon solvent. As noted previously, complexes containing less than 3.2 moles of alcohol are not stable at general ambient temperatures but must be heated in order to dissolve the complex. Once solvated by heating a metal compound of a metal selected from Groups IV-B and V-B of the Periodic Table of the Elements complex is added to the hot solvent. After the hot solvated complex and the metal compound are both in solution in the solvent, the heated solution can be carefully cooled to precipitate a uniform particle size product of less than 50 micron size consisting of a magnesium chloride precipitate, containing the selected second metal compound, which precipitate is useful as an alpha-olefin catalyst. This same procedure can be followed but omitting the second metal compound to produce a uniform particle size precipitate which can be recovered and separately contacted with a catalytic metal compound.

Magnesium chloride particles containing about 1.5 to 2.5 moles of alcohol of complexation per mole of magnesium can be treated with known agents to react with the alcohol and remove it in solution by washing out with hydrocarbon solvents. Generally, this is done before treatment with a IV-B or V-B compound as discussed in the preceding paragraph.

The magnesium metal used in the process of this invention can be in powder, chip or granular form. Magnesium metal stored for more than 6 months or exposed to air produces blackish product containing unreacted magnesium metal. Clean freshly produced magnesium metal, but without activation with iodine, produces, while suitable, a dark-grayish product containing more than 0.1% free unreacted metal. U.S. Pat. No. 2,287,088 discloses that suitable activators for alkaline earth metals such as calcium and magnesium are aluminum, mercuric salts, iodine or anhydrous stannic chloride. Iodine is preferred in the present process as it is effective in very small amounts. Activation with iodine is conducted between about 50° to about 200° C., preferably from about 70° C. to about 120° C. in refluxing hydrocarbon solvent for 1 to 4 hours using a maximum of up to 1 gram of iodine per mole of magnesium.

The amount of iodine used for activation of the magnesium is dependent on the size (exposed surface area) of magnesium metal. Fine powder, less than about 75 μm (No. 200 sieve), (ASTM E-11) needs about 0.5 grams of iodine per mole of magnesium metal, whereas chips need about 0.2 grams of iodine per mole of magnesium metal. The magnesium metal after activation with iodine can be washed in hydrocarbon solvent before the first reaction step, but washing is not critical.

The low boiling hydrocarbon ether free solvent-reaction medium used in the practice of this invention can be any aprotic hydrocarbon that is inert to the reaction. It is preferred that the hydrocarbon solvent be aliphatic, alicyclic or aromatic and have the same or a higher boiling point than the boiling point of the oxygen containing compound. The hydrocarbon solvent used can be selected from n-hexane and n-heptane, cyclohexane, methylcyclohexane, benzene, toluene, isoparaffinic hydrocarbon fractions such as Isopar E ™, Isopar G ™ or Isopar H ™ and other commonly used inert hydrocarbon solvents. The Isopar materials are isoparaffinic solvents whose characterizing properties are set forth in Table 3 below.

The alkyl halide used has the formula RX where X is halide, preferably chloride, and R is a radical of 1 to 20 carbon atoms, preferably an alkyl, of 1 to 8 carbon atoms or aryl or cycloalkyl radical of 3 to 8 carbon atoms, such as methyl chloride, ethyl chloride, butyl chloride, cyclohexyl chloride, and benzyl chloride and corresponding bromides and iodides.

The process was developed to prepare a soluble $MgCl_2$ in high concentration form; i.e., >1.0 molar solution, and preferably between 1.5 to 2.0 molar solution by using the following formula:

$$sM + mA + nC = x$$

where $1 < x < 2$ and x is expressed in moles. M=magnesium/$MgCl_2$, A=alcohol, C=chloro-alcohol compounds, $s = \leq 1.0$ mole, $m = \geq 0 \& \leq 3.0$ moles, $n = > 0 \& \leq < 6.0$ moles.

The following examples further illustrate the invention.

EXAMPLE 1

A round bottom three-necked 500 ml glass reactor equipped with a reflux condenser was charged under an argon atmosphere with 50 ml of dibutylmagnesium in n-heptane (0.8 density, 32.8% wt.) having 2.2 gm of magnesium in it, and 100 ml of n-heptane. This mixture was then chlorinated by bubbling under controlled conditions with about 7.0 gram of dry anhydrous hydrogen chloride. During chlorination with hydrogen chloride, the reaction slurry was maintained with good agitation. Temperature of the reaction slurry was raised to 40° C. and maintained. The slurry was then tested for total base and found to be close to neutral pH. Then, all released butane during the reaction was allowed to be distilled off and 2-methyl-1-pentanol was added slowly to the agitated reaction slurry until all solids were solubilized. A total of 35 ml of 2-methyl-1-pentanol was added. The resulting solution was clean and clear and was kept overnight at room temperature, then in the refrigerator at 10° C. for one day, with no precipitation of solids. The solution product was analyzed and showed 0.65 molar concentration of $MgCl_2$.

EXAMPLE 2

A round bottom three-necked 500 ml reaction flask equipped with a reflux condenser was charged under an argon atmosphere with 6.0 gm of magnesium metal (0.247M), 200 ml of n-heptane, and a few crystals of iodine. This mixture was heated to reflux temperature (98° C.) for sixty minutes to activate the metal. Then, 26 ml (22.85 gm) of n-BuCl was added over about twenty minutes to the metal slurry at reflux temperature. The resulting reaction mixture was allowed to reflux for sixty minutes, then heating was cut off and 9.0 gm of dry anhydrous hydrogen chloride was bubbled into the reaction mixture under good agitation at 70° C. or below. During the HCl addition, butane was released and allowed to be distilled off. Finally, a thick whitish reaction slurry was obtained.

To this slurry at 55° C., 90 ml of 2-methyl-1-pentanol was added under good agitation over a period of thirty minutes. Almost all solids were solubilized. The final reaction product slurry containing some suspended particles which were removed by filtration and the clean, clear filtrate was analyzed. The analysis indicated the product had 0.73 molar concentration of magnesium, and total base was found to be almost nil. The final solution product was found to be stable at room temperature.

EXAMPLE 3

Magnesium metal (12.3 gm, 0.506M) was placed in a three-necked round bottom reactor flask along with about 275 ml of n-heptane and 0.25 gm of iodine crystals. This mixture was heated to reflux temperature under argon atmosphere for about sixty minutes to activate the metal. Then, 53 ml (0.505M) n-BuCl was added in about twenty minutes to this metal slurry at reflux temperature. This resulting reaction mixture was allowed to react at reflux temperature for one hour. The reaction slurry was then cooled down to 45° C. and 20.6 gm (0.565M) of dry anhydrous hydrogen chloride was bubbled slowly through the slurry under good agitation. During this reaction, the temperature of the slurry increased quickly to 73° C. with the reflux of butane. After the hydrogen chloride reaction, the temperature of the slurry was raised to 95° C. by heating and simultaneous distillation of butane from the reaction slurry. Heating was then cut off, and 190 ml (1.536M) of 2-methyl-1-pentanol was added to the reaction slurry under good agitation. The solid was solubilized and the reaction mixture, containing some suspended grayish particles, was filtered hot. The filtrate, at 48°–50°, was clear. Analysis of this warm (50° C.) filtrate showed a 1.07M magnesium concentration. The filtrate was allowed to cool down and left overnight under stirring. By the next morning solids had been precipitated out of this solution (at 20° C.). The slurry was allowed to stand without stirring to permit settling of the solids and then the clear supernatant solution was analyzed for magnesium and found to have 0.73M magnesium concentration. One hundred fifty ml of this clean solution was siphoned into a bottle and remaining 350 ml of slurry containing solid was reacted with 25 ml of additional 2-methyl-1-pentanol. Within twenty minutes of stirring, all solids dissolved and was found to be stable at room temperature. Analysis of this solution showed it having about a 0.98M $MgCl_2$ concentration.

EXAMPLE 4

Anhydrous $MgCl_2$ (containing no base) (38.2 gm) having 20.1% wt. Mg made by reacting dibutyl magnesium (DBM) with HCl, filtered, washed and dried under argon gas was placed in a reaction bottle along with 320 ml of n-heptane under argon atmosphere. Then, 118 ml of 2-methyl-1-pentanol (2-MPOH) was added under good agitation over a thirty minute period. The solids were solubilized and the temperature of the solution was 38° C. On cooling to 20° C., the solution turned turbid, and another 7.0 ml of 2-MPOH was added under good agitation. Finally, all solid particles were dissolved and a clean solution was obtained which was stable at 20° C. or higher temperature. The analysis of the final solution showed 0.7 Molar $MgCl_2$.

EXAMPLE 5

Anhydrous $MgCl_2$ (containing no base) (20.0 gm, 0.1654M) containing 20.1% Mg made from dibutyl magnesium (DBM) by reaction with HCl, washed and argon dried, was placed in a three-necked round bottom flask under argon atmosphere, along with 200 ml of n-heptane and heated to 75° C. Then, 42 gm (0.4118M) of 2-methyl-1-pentanol (2-MPOH) was added to the slurry. All solid anhydrous $MgCl_2$ solubilized at 73°–75° C. The clear solution (73° C.) was then cooled to room temperature and kept overnight under slow stirring. During cooling, the solution turned turbid and became thicker by the time the temperature dropped to 25° C. Stirring overnight at 25° C. and below was maintained to attain equilibrium. The next morning the slurry was filtered to remove solids. The clear filtrate was analyzed for Mg and traces were found (a few ppm). The solid was washed with solvent and dried. The final weight of dried solid was about 60 gm. Analysis of the dry solid showed it having 6.7% Mg, 19.539% Cl, and 70.72% 2-MPOH (2-methyl-1-pentanol).

EXAMPLE 6

The following test was done to determine the nature of the product obtained on concentrating a solution of a soluble $MgCl_2$ product of this invention in n-heptane containing 3.2 moles of 2-MPOH per mole of $MgCl_2$ by heating at a high temperature under reduced pressure.

A soluble $MgCl_2$ product in solution in n-heptane (66.5 gm) having 2.27% wt. Mg, 6.625% Cl, 30.48% 2-MPOH, and 60.62% n-heptane prepared according to Example 4 above was placed in a round bottom evaporating flask under argon atmosphere. The solution was concentrated first by stripping n-heptane (most of it) at ambient temperature under reduced pressure from the flask. The solution turned more viscous when most of the n-heptane was removed. Then, the solution was concentrated further by heating slowly (40°–100° C.) under reduced pressure. After two hours at 90° C., the solution had become a semi-liquid-solid and on cooling turned to a glassy solid. It was again heated to 100° C. and turned into a thick, honey-like, viscous solution. Heating was continued up to 110° C. for one more hour, and after one hour at 110° C. some solid formation was seen; it was then cooled to room temperature. The product turned into a glassy, flake type, clear solid. The final weight of the product was 15.5 gm containing 9.74% wt. Mg, 28.40% Cl, and 61.86% 2-MPOH.

EXAMPLE 7

Magnesium metal (48.62 gm, 2.0M) chips were placed in a three-necked round bottom glass reactor, along with 1500 ml of n-heptane and 1.0 gm of iodine crystals under argon atmosphere. This mixture was heated to reflux temperature (98° C.) for one hour to activate the metal. Then, 100 ml of 1.35M 2-methylpentyloxymagnesium solution containing 0.4 mole 2-MPOH per mole of 2-MPOMgCl in heptane was added to the slurry for initiation of a fast reaction. Thereafter, about 750 ml (612.0 gm) of 2-methyl-1-pentanol (2-MPOH) was added at the rate of about 8–10 ml per minute. During addition of 2-MPOH, dry anhydrous hydrogen chloride was also bubbled through the mixture. The reaction was continued at reflux temperature initially and then dropped to 85° C. by cutting off heating. The reaction of Mg metal was very fast, even at 85° C. Finally, the reaction temperature was maintained at 70° C. and hydrogen chloride addition was continued for about three hours. During these three hours of reaction, a total of 156 gm of dry anhydrous hydrogen chloride was added. Finally, in about four hours of reaction, all the metal chips were reacted and dissolved. Finally, the reaction slurry containing some gray suspended particles was stirred overnight under an argon atmosphere without heating. The next morning the reaction slurry contained a snow white solid and the slurry temperature was 22° C. This reaction slurry was then heated to 70° C. and all solids dissolved to obtain a clear, colorless, solution with no gray particles. A sample of this product was analyzed for total base and it was found that the reaction liquid needed a total of 0.15M HCl (5.5 gm) to obtain a neutral product. Then, about 7.0 gm of HCl (0.19M) was bubbled into the reaction liquid to complete chlorination. The reaction liquid was then stirred for about one hour at 70° C. and confirmed that it does not have any base, and it was found to be neutral in pH. The reaction product-solution (70° C.) was then cooled using a water bath with slow stirring (60–80 RPM) of the product mixture. Solid particles started forming at 55° C. The slurry was slowly stirred at 25° C. for two hours, and then part of this slurry was filtered to obtain a solid and a liquid product. The solid product was washed with pentane and dried with argon gas at room temperature. The dry solid product was snow white, fine, and of uniform particle size ($<50\mu$). Dried solids and first filtrate (without wash) were sampled and analyzed. Analyses are shown in Table I-A.

The remaining slurry was then heated to 70° C. and a clear solution was obtained; then 14 ml (23.5 gm) of titanium tetrachloride ($TiCl_4$) was added to it drop-by-drop under good agitation. This reactant liquid which was clear at 70° C. turned into a thick slurry containing a slimy solid up on cooling to ambient temperature (26° C.). This slurry was difficult to filter, therefore one mole (124 ml) of 2-MPOH was added to it while heating the slurry back up to 70° C., at which temperature all solids solubilized. On cooling this clear solution to 25° C. under slow agitation, it turned into a slurry containing good white color and uniform particle size solids. After about sixty minutes stirring at 25° C., the slurry was filtered to obtain solid and liquid samples for analysis. The solid was washed with pentane and dried by passing argon gas through the product overnight. Analysis of the solid and liquid samples is shown in Table I-B.

TABLE I-1

|  | Weight Percent | | | | Mole 2-MPOH | |
| --- | --- | --- | --- | --- | --- | --- |
|  | Mg | Ti | Cl | 2-MPOH | n-heptane | Mole Mg |
| ASolid | 6.3 | <0.0001 | 18.37 | 74.34 | 0.98 | 2.81 |
| Filtrate | 0.69 | <0.0001 | 2.01 | 6.90 | 90.46 | 2.41 |
| BSolid | 6.60 | 0.0570 | 19.41 | 70.72 | 3.21 | 2.55 |
| Filtrate | 0.79 | 0.44 | 3.56 | 22.32 | 72.87 | 6.73 |

The solid particulate products A and B were tested by the Brunauer, Emmett and Teller (BET) method for determining surface area. See Brunauer, S., Emmett, P. H., and Teller, E., "Adsorption of Gases in Multimolecular Layers," Journal of the American Chemical Society, JACSA, Vol. 60, 1938, pp. 309–319 or ASTM C819-77 Standard Test Method for Specific Surface Area of Carbon or Graphite. A scanning electron microscope (SEM) was used to determine the morphology and particle sizes of these products. The surface area, particle size distribution and average particle size of the particulate products are reported in Table I-2.

TABLE I-2

| | BET | SEM | |
| --- | --- | --- | --- |
| Sample | Surface Area $M^2/g$ | Particle Size Range $\mu m$ | Average Particle Size $\mu m$ |
| A | 1.8(1) 2.3(2) | <0.5–13 | 8 |
| B | 1.7(1) 4.4(2) | <0.1–25 | 12 |

(1) Samples degassed at 133.3 Pa (Pascals) at 25° C. for 24 hours
(2) Samples degassed at 133.3 Pa at 55° C. for 24 hours

EXAMPLE 8

A. Sixty gm of $MgCl_2$:2.5 2-MPOH solid (6.7% Mg) prepared according to Example 5 was placed in a reaction flask under argon atmosphere, along with 200 ml of n-heptane. This mixture was then heated to 70° C. to obtain clear solution, and then 2.5 gm (0.0132M) $TiCl_4$ was added with good agitation. A clear solution was obtained at 73° C., and then 25 ml of 2MPOH was added (total) to it, and it was cooled to room temperature. Then, it was cooled to 15° C. and no solid was found. The solution was stable and clear.

B. To this solution was added an additional 2.5 gm (0.0132M) $TiCl_4$; a solid particulate product was formed which was not soluble at room temperature; therefore, 10 ml 2MPOH was added gradually to solubilize the solid, and a clean stable solution was obtained at 25° C.

EXAMPLE 9-A

Anhydrous $MgCl_2$ (1.96 gm) was placed in a 100 ml flask under argon atmosphere along with 50 ml of n-heptane. This mixture was then heated to 50° C. and then 4.72 ml of 2-ethoxyethanol was added gradually under good agitation over a period of fifteen minutes. The solid did not dissolve; therefore, 1.5 ml of 2-(2-chloroethoxy)ethanol was added gradually under good agitation at 50° C., and within fifteen minutes at 50° C. all the solids were solubilized. Two distinct liquid layers were formed. The reaction flask was then cooled to 25° C. and kept at room temperature for three days. No precipitation of solids occurred. The top layer and the bottom layer of the clean, clear liquid were analyzed for magnesium. The top layer was found to contain no magnesium, whereas the bottom layer was rather fluid but oily in nature and had analyzed about 1.95M Mg.

The solution having two layers was then concentrated by distilling off the solvent and possibly some alcohol/alcohol derivatives (chloro-alcohol) under reduced pressure and slow, gradual heating. Finally, it was concentrated at 100° C. under reduced pressure for one hour and then cooled to 20° C. The product turned into a glassy solid. It was indicated that, possibly by spray drying under reduced pressure at higher temperature, round uniform particles could be made.

EXAMPLE 9-B

Example 9-A was repeated using about 4.7⅔ ml of 2-ethoxyethanol and 0.5 ml of 2-(2-chloroethoxy) ethanol and heating to the reflux temperature of the solvent. The resulting solution was carefully cooled with slow agitation as described in Example 7 to precipitate uniform particle solids.

EXAMPLE 9-C

Example 9-B was repeated except once the magnesium chloride was in solution 1 mole of titanium per 10 moles of magnesium chloride was added to the solution and then followed by again carefully cooling the solution with slow agitation as described in Example 7 to precipitate white uniform titanium containing particles.

EXAMPLE 10

Using the procedure of Example 9, 1.85 gm of $MgCl_2$ slurry in n-heptane (50 ml) was treated with 5 ml of 2-methyl-1-butanol at 50° C., but the solid did not dissolve. Then, 1.5 ml of 2-(2-chloroethoxy)ethanol was gradually added, and in thirty minutes stirring at 50° C., all the solids dissolved and formed two layers at liquid. The top layer contained no magnesium, whereas the bottom layer contained all the magnesium.

EXAMPLES 11–21

Examples 11–21 were also carried out using the procedure of Example 9, various quantities of $MgCl_2$ were reacted with various combinations of oxygen-containing compounds such as ethanol, 2-ethyl-1-hexanol, 2-ethylcyclohexanol, 2,3-dimethyl-2-butanol, 3-methyl-2-butanol, and chlorohydrin compounds such as 2-chloroethanol, 2-(2-chloroethoxy)ethanol and 2-[(2-chloroethoxy)ethoxy]ethanol.

Results of all these examples are shown in Table II.

TABLE II

Solubility of $MgCl_2$ by Using Chloro-Alcohols

| Ex. # | Reactants | Moles | Solvent | Results/Remarks |
| --- | --- | --- | --- | --- |
| 11 | Anhyd. $MgCl_2$ | 1 | | Soluble, stable at 25° C. & more. |
| | 2-E-EtOH[1] | 3 | n-heptane | Two distinct liquid layers. |
| | 2-(2-Chloroethoxy)-ethanol | 2 | | Top layer contained no Mg. Bottom layer contained 1.8 M Mg concentration. |
| 12 | Anhyd. $MgCl_2$ | 1 | | Soluble & stable at 25° C. & above. |
| | 2-Methyl-1-butanol | 3 | n-heptane | Forms two distinct layers. |
| | 2-(2-Chloroethoxy)- | 2 | | Top layer contained no Mg. |

TABLE II-continued

Solubility of $MgCl_2$ by Using Chloro-Alcohols

| Ex. # | Reactants | Moles | Solvent | Results/Remarks |
|---|---|---|---|---|
|  | ethanol |  |  | Bottom layer contained about 1.8 M Mg concentration. |
| 13 | Anhyd. $MgCl_2$ | 1 |  | Top layer contained no Mg. |
|  | Ethanol | 2.7 | n-heptane | Bottom layer contained ~1.9 M |
|  | 2-(2-Chloroethoxy)-ethanol | 3.7 |  | Mg concentration. |
| 14 | Anhyd. $MgCl_2$ | 1 |  | Top layer contained no Mg. |
|  | 2-Ethoxy EtOH | 1.64 | n-heptane | Bottom layer contained ~1.8 M |
|  | 2-Chloroethanol | 4.80 |  | Mg concentration. |
| 15 | Anhyd. $MgCl_2$ | 1 |  | Top layer contained no Mg. |
|  | Ethanol | 1.3 | n-heptane | Bottom layer contained ~1.5 M |
|  | 2-(2-Chloroethoxy)- | 5.0 |  | Mg concentration. |
| 16 | Anhyd. $MgCl_2$ | 1 |  | Top layer contained no Mg. |
|  | 2-Ethyl cyclohexanol | 3 | n-heptance | Bottom layer contained 1.5 M |
|  | 2-Chloroethanol | 2 |  | Mg concentration. |
| 17 | Anhyd. $MgCl_2$ | 1 |  | Top layer contained no Mg. |
|  | 2,3-dimethyl-2-butanol | 3 | n-heptane | Bottom layer contained 1.8 M Mg concentration. |
|  | 2-(2-Chloroethoxy)-ethanol | 1.5 |  |  |
| 18 | Anhyd. $MgCl_2$ | 1 |  | Top layer contained no Mg. |
|  | 2-(2-Chloroethoxy)-ethanol | 5.6 | n-heptane | Bottom layer contained 1.7 M |
| 19 | Anhyd. $MgCl_2$ | 1 |  | Top layer contained no Mg. |
|  | 3-Methyl-2-butanol | 3 | n-heptane | Bottom layer contained 1.8 M |
|  | 2-[2-(2-Chloro-ethoxy)ethoxy]-ethanol | 1.3 |  | Mg concentration. |
| 20 | Anhyd. $MgCl_2$ | 1 |  | Top layer contained no Mg. |
|  | 2-Ethoxyethanol | 3 | n-heptane | Bottom layer contained 1.7 M |
|  | 2-[2-(2-Chloro-ethoxy)ethoxy] EtOH | 1.3 |  | Mg concentration. |
| 21 | Anhyd. $MgCl_2$ | 1 |  | Top layer contained no Mg. |
|  | 2-MPOH | 2 | n-heptane | Bottom layer contained 1.60 M |
|  | 2-[2-(2-Chloro-EtO)EtO]EtOH | 2.5 |  | Mg concentration. |

What is claimed:

1. A process for producing a magnesium halide alcohol complex, comprising: reacting in an ether free hydrocarbon reaction medium, a reactant selected from magnesium metal, dialkyl magnesium, alkyl magnesium halide, alkyl magnesium alkoxide, magnesium dialkoxide and alkoxy magnesium halide with an anhydrous hydrogen halide in the presence of up to six moles of a chlorosubstituted alcohol containing 1 to 10 carbon atoms per mole of magnesium halide.

2. The process of claim 1 wherein the chloro-substituted alcohol is used in a mixture with an alcohol selected from beta-alkyl substituted primary, secondary or tertiary alcohols of 5 to 20 carbon atoms and unsubstituted primary monohydric alcohols of 1 to 20 carbon atoms, in proportions represented by the formula: $sM+mA+nC=x$ where $1<x<2$ and x is expressed in moles, and wherein M is a magnesium dihalide, A is selected from beta-alkyl substituted primary, secondary and tertiary alcohols of 5 to 20 carbon atoms and unsubstituted primary alcohols of 1 to 10 carbon atoms and C is a chloro-substituted alcohol of 1 to 10 carbon atoms and in which formula s is less than or equal to one mole, m is equal to or greater than zero and less than or equal to three moles and n is greater than zero and equal to or less than six moles.

3. The process of claim 1 wherein the reactant selected is a dialkyl magnesium which is reacted with a dry hydrogen halide and an alcohol selected from chloro-substitiued alcohols and mixtures of chloro-substituted alcohols and beta-alkyl substituted alcohols.

4. The process of claim 1 wherein magnesium metal is reacted with a dry hydrogen halide in the presence of a $C_1$–$C_{10}$ chloro-substituted alcohol.

5. The process of claim 2 wherein the dialkyl magnesium compound is prepared in situ in the hydrocarbon reaction medium by reacting magnesium metal with an alkyl halide of 1 to 8 carbon atoms; the dialkyl magnesium compound is then reacted with a dry hydrogen halide and a $C_1$–$C_{10}$ chloro-substituted alcohol.

6. The process of claim 1 wherein a di(beta-alkyl substituted alkoxy) magnesium compound is reacted with a dry hydrogen halide in the presence of a chloro-substituted alcohol.

7. The process of claim 1 wherein a beta-alkyl substituted alkoxy magnesium chloride is reacted with a dry hydrogen halide in the presence of a chloro-substituted alcohol.

8. A process for producing an alcohol complexed hydrocarbon soluble magnesium chloride comprising reacting, in an ether free hydrocarbon medium, a reactant selected from magnesium metal, anhydrous magnesium chloride, dialkylmagnesium, dialkoxy magnesium and alkoxy magnesium chloride with a dry hydrogen halide and a $C_1$–$C_{20}$ monohydric normal alcohol followed by the addition of a $C_1$–$C_{10}$ chloro-alcohol.

9. The process of claim 7 wherein the selected reactant, dialkyl magnesium, is reacted simultaneously with a dry hydrogen halide and a $C_1$–$C_{10}$ monohydric alcohol followed by addition of a $C_1$–$C_{10}$ chloro-alcohol.

10. The process of claim 7 wherein magnesium metal is reacted with a dry hydrogen halide and a $C_1$–$C_6$ alkyl halide in the presence of a $C_1$–$C_{10}$ chloro-alcohol.

11. The process of claim 9 wherein the reaction of the magnesium metal, hydrogen halide and alkyl halide are conducted in the presence of both a $C_1$–$C_{20}$ monohydric normal alcohol and a $C_1$–$C_{10}$ chloro-alcohol.

12. The process of claim 7 wherein the dialkyl magnesium compound is prepared in situ in the hydrocarbon reaction medium by reacting magnesium metal with an alkyl halide of 1 to 8 carbon atoms; the dialkyl magnesium compound is then simultaneously reacted with a $C_1$–$C_{20}$ monohydric normal alcohol followed by addition of a $C_1$–$C_{10}$ chloro-alcohol.

13. The process of claim 7 wherein anhydrous magnesium chloride is reacted with a $C_1$–$C_{20}$ monohydric normal alcohol and a $C_1$–$C_{10}$ chloro-alcohol.

14. The process of claim 7 wherein a reactant selected from alkoxy magnesium chloride, alkyl magnesium chloride and mixtures thereof is reacted with a dry hydrogen halide with the simultaneous addition of a $C_1$–$C_{20}$ monohydric normal alcohol followed by the addition of a $C_1$–$C_{10}$ chloro-alcohol.

15. The process of claim 7 wherein magnesium metal is reacted with a dry hydrogen halide in the presence of a $C_1$–$C_{20}$ monohydric normal alcohol followed by the addition of a $C_1$–$C_{10}$ chloro-alcohol.

16. The process of claim 7 wherein the reactant selected is a magnesium dialkoxide which is reacted with dry hydrogen halide followed by the addition of a $C_1$–$C_{10}$ chloro-alcohol.

17. The process of claims 2 or 3 wherein the dry hydrogen halide is hydrogen chloride and the amount of the beta-alkyl substituted alcohol is not greater than three moles per mole of magnesium chloride.

18. The process of claims 2 or 3 wherein the dry hydrogen halide is hydrogen chloride and the amount of the beta-alkyl substituted alcohol is at least 3.2 moles per mole of magnesium chloride.

19. A process for producing a particulate, solid magnesium dihalide alcohol complex comprising: reacting in an ether free hydrocarbon reaction medium a reactant selected from magnesium metal, dialkylmagnesium, alkylmagnesium halide, alkyl magnesium alkoxide, magnesium dialkoxide and alkoxymagnesium halide with an anhydrous hydrogen halide in the presence of 1.5 to 5 moles of an alcohol selected from $C_1$ to $C_{10}$ chloro-substituted alcohols, $C_5$ to $C_{18}$ beta-alkyl substituted alcohols, mixtures of the $C_1$ to $C_{10}$ chloro-substituted alcohol with the $C_5$ to $C_{18}$ beta-alkyl substituted alcohols, mixtures of $C_1$ to $C_{10}$ chloro-substituted alcohols with $C_1$ to $C_{20}$ monohydric alcohols, mixtures of $C_5$ to $C_{18}$ beta-alkyl substituted alcohols with $C_1$ to $C_{20}$ monohydric normal alcohols and mixtures of $C_1$ to $C_{10}$ chloro-substituted alcohols, $C_5$ to $C_{18}$ alkyl substituted alcohols and $C_1$ to $C_{20}$ monohydric normal alcohols (per mole of magnesium dihalide) to form the magnesium dihalide alcohol complex, heating the reaction mixture to dissolve the complex, cooling the solution with controlled agitation to produce a solid particulate product.

20. The process of claim 19 in which 1.5 to 3 moles of total alcohol are employed per mole of magnesium dihalide.

21. The process of claim 19 in which 1.5 to 2.5 moles of total alcohol are employed per mole of magnesium dihalide.

22. The process of any of claims 19, 20 or 21 wherein the alcohol is a $C_1$ to $C_{10}$ chloro-substituted alcohol selected from 3-chlorobenzynol, 2-chlorobenzynol, 4-chlorobenzynol, 4-chloro-1-butanol, 2-chlorocyclohexanol, 3-chloro-2-2-dimethyl-1-propanol, 2-chloroethanol, 2-(2-chloroethoxy)ethanol, 2-[2-(2-chloroethoxy)ethoxy]ethanol, 2-chlorophenol, 2-chlorophenethyl alcohol, 1-chloro-2-propanol, 2-chloro-1propanol, 3-chloro-1-propanol, and mixtures thereof.

23. The process of any of claims 19, 20 or 21 in which the alcohol is a beta-alkyl substituted alcohol selected from 2-methyl-1-pentanol, 2-methyl-1-butanol, 2-ethyl-1-butanol, 2-ethyl-1-pentanol, 2-ethyl-1-hexanol, 2-ethyl-4-methyl-1-pentanol, 2-propyl-1-heptanol, 2-methyl-1-hexanol, 2-ethyl-5-methyl-1-octanol, 2,2-dimethyl-1-octanol, and the like, or mixtures thereof.

24. The process of any of claims 19, 20, 21, 22 or 23 wherein a compound of a metal selected from Groups IV-B and V-B is dissolved in the reaction solution before the reaction solution is cooled to produce solid particulate product.

25. The process of claim 24 wherein the metal compound is a titanium compound of the formula $$Ti(OR)_y X_{4-y}$$

wherein R is an alkyl, aryl or aralkyl group having 1 to 24 carbon atoms, X is halogen and Y is zero to four.

26. The process of claim 24 wherein the compound of a metal selected from Groups IV-B and V-B is a titanium compound selected from titanium tetrachloride, titanium tetrabromide, titanium tetraiodide, monoethoxytrichlorotitanium, dimethoxydichlorotitanium, trimethoxymonochlorotitanium, tetramethoxytitanium, monoethoxytrichlorotitanium, diethoxydichlorotitanium, triethoxymonochlorotitanium, tetraethoxytitanium, monoisopropoxytrichlorotitanium, diisopropoxydichlorotitanium, triisopropoxymonochlorotitanium, tetraisopropoxytitanium, monobutoxytrichlorotitanium, dibutoxydichlorotitanium, monopentoxytrichlorotitanium, monophenoxytrichlorotitanium, diphenoxydichlorotitanium, triphenoxymonochlorotitanium and tetraphenoxytitanium.

27. A catalyst support product prepared by the steps of:
(a) reacting in an ether free hydrocarbon reaction medium a reactant selected from magnesium metal, dialkylmagnesium, alkylmagnesium halide, alkyl magnesium alkoxide, magnesium dialkoxide and alkoxymagnesium halide with an anhydrous hydrogen halide in the presence of 1.5 to 5 moles of an alcohol selected from $C_1$ to $C_{10}$ chloro-substituted alcohols, $C_5$ to $C_{18}$ betaalkyl substituted alcohols, mixtures of the $C_1$ to $C_{10}$ chloro-substituted alcohol with the $C_5$ to $C_{18}$ beta-alkyl substituted alcohols, mixtures of $C_1$ to $C_{10}$ chloro-substituted alcohols with $C_1$ to $C_{20}$ monohydric alcohols, mixtures of $C_5$ to $C_{18}$ beta-alkyl substituted alcohols with $C_1$ to $C_{20}$ monohydric normal alcohols and mixtures of $C_1$ to $C_{10}$ chloro-substituted alcohols, $C_5$ to $C_{18}$ alkyl substituted alcohols and $C_1$ to $C_{20}$ monohydric normal alcohols (per mole of magnesium dihalide) to form the magnesium dihalide alcohol complex,
(b) heating the reaction mixture to dissolve the complex,
(c) cooling the solution with controlled agitation to produce a solid particulate product having an average particle size distribution of less than 100 μm; and
(d) recovering the solid particulate catalyst support.

28. A supported catalyst product prepared by the steps of:
(a) reacting in an ether free hydrocarbon reaction medium containing a compound of a metal selected from Groups IV-B and V-B dissolved therein, a reactant selected from magnesium metal, dialkylmagnesium, alkylmagnesium halide, alkyl magnesium alkoxide, magnesium dialkoxide and alkoxymagnesium halide with an anhydrous hydrogen halide in the presence of 1.5 to 5 moles of an alcohol selected from $C_1$ to $C_{10}$ chloro-substituted alcohols, $C_5$ to $C_{18}$ beta-alkyl substituted alcohols, mixtures of the $C_1$ to $C_{10}$ chloro-substituted alcohol with the $C_5$ to $C_{18}$ beta-alkyl substituted alcohols, mixtures of $C_1$ to $C_{10}$ chloro-substituted alcohols with $C_1$ to $C_{20}$ monohydric alcohols, mixtures of $C_5$ to $C_{18}$ beta-alkyl substituted alcohols with $C_1$ to $C_{20}$ monohydric normal alcohols and mixtures of $C_1$ to $C_{10}$ chlorosubstituted alcohols, $C_5$ to $C_{18}$ alkyl substituted alcohols and $C_1$ to $C_{20}$ monohydric normal alcohols (per mole of magnesium dihalide) to form the magnesium dihalide alcohol complex,
(b) heating the reaction mixture to dissolve the complex,
(c) cooling the solution with controlled agitation to produce a solid particulate product having an average particle size distribution of less than 100 μm; and
(d) recovering the solid particulate catalyst support.

29. The product of claim 27 or 28 in which 1.5 to 3 moles of total alcohol are employed per mole of magnesium dihalide.

30. The product of claim 27 or 28 in which 1.5 to 2.5 moles of total alcohol are employed per mole of magnesium halide.

31. The product of claim 27 or 28 wherein 1.5 to 3.0 moles of total alcohol are employed per mole of magnesium halide and the alcohol is a $C_1$ to $C_{10}$ chloro-substituted alcohol selected from 3-chlorobenzynol, 2-chlorobenzynol, 4-chlorobenzynol, 4-chloro-1-butanol, 2-chlorocyclohexanol, 3-chloro-2-2-dimethyl-1-propanol, 2-chloroethanol, 2-(2-chloroethoxy)ethanol, 2-[2-(2-chloroethoxy)ethoxy]ethanol, 2-chlorophenol, 2-chlorophenethyl alcohol, 1-chloro-2-propanol, 2-chloro-1-propanol, 3-chloro-1-propanol, and mixtures thereof.

32. The product of claim 27 or 28 in which the alcohol is a beta-alkyl substituted alcohol selected from 2-methyl-1-pentanol, 2-methyl-1-butanol, 2-ethyl-1-butanol, 2-ethyl-1-pentanol, 2-ethyl-1-hexanol, 2-ethyl-4-methyl-1-pentanol, 2-propyl-1-heptanol, 2-methyl-1-hexanol, 2-ethyl-5-methyl-1-octanol, 2,2-dimethyl-1-octanol, and the like, or mixtures thereof.

33. The product of claim 28 wherein the metal compound is a titanium compound of the formula $$Ti(OR)_y X_{4-y}$$

wherein R is an alkyl, aryl or aralkyl group having 1 to 24 carbon atoms, X is halogen and Y is zero to four.

34. The product of claim 33 wherein the compound of a metal selected from Groups IV-B and V-B is a titanium compound selected from titanium tetrachloride, titanium tetrabromide, titanium tetraiodide, monoethoxytrichlorotitanium, dimethoxydichlorotitanium, trimethoxymonochlorotitanium, tetramethoxytitanium, monoethoxytrichlorotitanium, diethoxydichlorotitanium, triethoxymonochlorotitanium, tetraethoxytitanium, monoisopropoxytrichlorotitanium, diisopropoxydichlorotitanium, triisopropoxymonochlorotitanium, tetraisopropoxytitanium, monobutoxytrichlorotitanium, dibutoxydichlorotitanium, monopentoxytrichlorotitanium, monophenoxytrichlorotitanium, diphenoxydichlorotitanium, triphenoxymonochlorotitanium and tetraphenoxytitanium.

35. The product of claim 27 or 28 wherein the average particle size distribution is between 0.1 and 50 μm.

36. The product of claim 27 or 28 wherein the average particle size distribution is between 0.1 to 25 μm.

37. The product of claim 27 or 28 wherein the average particle size distribution is between 5 and 15 μm.

* * * * *